United States Patent [19]

Monget et al.

[11] Patent Number: 5,434,056
[45] Date of Patent: Jul. 18, 1995

[54] METHOD OF BACTERIOLOGICAL ANALYSIS, AND MEDIUM FOR THE DETECTION OF BACTERIA OF THE SALMONELLA GENUS

[75] Inventors: Daniel Monget, Saint Sorlin en Bugey; Francois Villeval, Saint Genis les Ollieres, both of France

[73] Assignee: Bio Merieux, Marcy L'Etoile, France

[21] Appl. No.: 247,461

[22] Filed: May 23, 1994

Related U.S. Application Data

[63] Continuation of Ser. No. 920,372, filed as PCT/FR91/01075, Dec. 26, 1991, abandoned.

[30] Foreign Application Priority Data

Dec. 28, 1990 [FR] France ................ 90 16635

[51] Int. Cl.$^6$ ............... C12Q 1/54; C12Q 1/34; C12Q 1/04; C12Q 1/24
[52] U.S. Cl. .................... 435/14; 435/34; 435/4; 435/7.35; 435/7.32; 435/29; 435/18; 435/30; 435/810; 435/975
[58] Field of Search ............ 435/14, 4, 7.32, 7.2, 435/7.35, 7.72, 30, 34, 38, 18, 25, 29, 810, 975; 514/2

[56] References Cited

U.S. PATENT DOCUMENTS

| | | | |
|---|---|---|---|
| 3,856,628 | 12/1974 | Sbarra | 435/38 |
| 3,957,584 | 5/1976 | Kronish et al. | 435/18 |
| 4,010,078 | 3/1977 | Taylor | 435/38 |
| 4,070,247 | 1/1978 | Burt | 435/38 |
| 4,591,554 | 5/1986 | Koumura et al. | 435/18 |
| 4,603,108 | 7/1986 | Bascomb | 435/25 |
| 4,762,824 | 8/1988 | Kallenius et al. | 514/2 |
| 4,925,789 | 5/1990 | Edberg | 435/38 |

FOREIGN PATENT DOCUMENTS

| | | |
|---|---|---|
| 0214340 | 3/1987 | European Pat. Off. . |
| 0282733 | 9/1988 | European Pat. Off. . |
| 8603207 | 4/1986 | Spain . |
| 1459247 | 9/1990 | U.S.S.R. . |

OTHER PUBLICATIONS

Rambach, A; Applied & Environ. Microbio, Jan. 1990, pp. 301–303.
Davis et al, Microbiology (4th Edition) (1990) pp. 564–565.
Wu, William G., Medical Microbio, (2nd Edition) (1989) p. 348.

Primary Examiner—David A. Redding
Assistant Examiner—Louise N. Leary
Attorney, Agent, or Firm—Oliff & Berridge

[57] ABSTRACT

The invention relates to a method of bacteriological analysis for the selective detection of Salmonella and a medium for its implementation.

The method is based on the specific capacity of Salmonella to ferment glucuronic acid or one of its salts, and not to produce $\beta$-galactosidase.

The medium comprises a nutrient which is metabolized by the bacteria, a chromogenic or fluorigenic compound capable of being hydrolyzed by the enzyme $\beta$-galactosidase, glucuronic acid or one of its salts and a pH indicator.

23 Claims, No Drawings

METHOD OF BACTERIOLOGICAL ANALYSIS, AND MEDIUM FOR THE DETECTION OF BACTERIA OF THE SALMONELLA GENUS

This is a continuation of application Ser. No. 07/920,372 filed as PCT/FR91/01075, Dec. 26, 1991, now abandoned.

BACKGROUND OF THE INVENTION

The present invention relates to the characterization or isolation of bacteria of the Salmonella genus, by inoculating a specific culture medium with an inoculum presumed to contain said bacteria, growing the latter on the culture medium and developing one or more chromogenic or fluorigenic characterization phenomena using one or more biochemical characteristics which are specific to the bacteria sought.

Salmonella bacteria are Gram-negative enterobacteria which generally exhibit the following biochemical characteristics:
lactose—
ONPG—
urease—
$H_2S+$ No biochemical characteristic exists which can be attributed solely to the Salmonella genus, so the characterization of these bacteria generally requires the use of a plurality, or even a large number of biochemical tests, supplemented, where appropriate, by immunological tests or morphological examinations.

DESCRIPTION OF THE PRIOR ART

However, agar media, which are presented as being selective for Salmonella and which use at least two biochemical tests, each based on the presence or absence of a color, are commercially available.

These media generally contain inhibitors of Gram-positive bacteria and certain Gram-negative bacteria. Among the inhibitors commonly used, there may be mentioned bile salts (sodium deoxycholate and the like), sodium citrate and brilliant green.

The detection of Salmonella on these media is possible by virtue of:

the absence of fermentation of one or more carbohydrates (lactose and the like)

the investigation of the production of $H_2S$, a biochemical characteristic generally present in Salmonella; this detection is performed by incorporating sodium thiosulfate and a ferric salt into the medium.

The principal agar media used for the detection of Salmonella are:
D.C.L. agar from Société Diagnostics Pasteur
D.C.L.S. agar from Sociétés BioMérieux and Diagnostics Pasteur
Hektoen agar from Sociétés BioMérieux and Diagnostics Pasteur
S.S. agar from Sociétés BioMérieux and Diagnostics Pasteur
Kristensen agar from Société Diagnostics Pasteur
XLD agar from Sociétés BioMérieux and Diagnostics Pasteur.

However, these media have certain limitations linked to the principle for the characterization of Salmonella: any colorless colony (no carbohydrate fermentation) and/or any colony with a black center ($H_2S$ production) should be considered as suspect.

These media are in fact not very specific for Salmonella. Indeed, some species can develop and produce colonies having the same characteristics as those of Salmonella:

colorless colonies (lactose (—)):
Salmonella
Shigella
Serratia
Yersinia
*Hafnia alvei*
*E. coli* subsp. alkalescens dispar
*Morganella morganii*
*Proteus rettgeri* colonies with a black center ($H_2S$ (+)):
Salmonella
Citrobacter
*Proteus vulgaris*
*Proteus mirabilis*

Moreover, the production of $H_2S$ on these media is not always constant. These variations may be linked to various factors such as pH, concentration of oxygen around the colonies and the like.

Thus, a large number of Salmonella colonies do not exhibit the $H_2S$-positive character and, as a result, do not have a black center and remain colorless.

This results in a large number of unnecessary confirmations using "biochemical identification galleries" and agglutinant sera, leading to loss of time and increasing the cost of the examination.

Finally, the lack of a specific stain for Salmonella may be a source of errors. It is in fact very easy to miss a suspect colony. This is all the more true when the colonies are colorless or have the same color as that of the medium.

In other words, all these media do not by themselves provide sufficient reliability for the detection of Salmonella, on the one hand because of the nondistinctive colors used to indicate the presence of these bacteria and, on the other hand, because of the host of color phenomena or configurations capable of characterizing the presence of these bacteria.

In conformity with the publication:

New plate medium for facilitated differentiation of Salmonella spp. from Proteus spp. and other enteric bateria - Alain RAMBACH, Applied and Environmental Microbiology, Jan. 1990, 56, p. 301-303 a medium for the culture and selective detection of bacteria of the Salmonella genus has been proposed comprising:

a nutrient which is metabolized by the said bacteria a chromogenic compound which is capable of being hydrolyzed by the β-galactosidase enzyme produced by the bacterium, for developing a color, in this case 5-bromo-4-chloro-3-indolyl β-D-galactopyranoside which develops a blue color under the effect of its enzymatic hydrolysis by β-galactosidase propylene glycol with a pH indicator such as neutral red.

In this case, the principal biochemical test used for the detection of Salmonella consists in the acidic fermentation of propylene glycol by these bacteria, the said fermentation being detected with neutral red. And this principal test is complemented by that of β-galactosidase, this enzyme being absent in Salmonella which therefore do not hydrolyze the chromogenic compound.

In total, the following range of colors may give the interpretation below:

brilliant red: presence of propylene glycol+ and β-galactosidase — bacteria, therefore presence of Salmonella blue: presence of propylene glycol — and β-galactosidase+ bacteria, therefore absence of Salmonella violet: presence of propylene glycol+ and β-galactosidase+ bacteria, therefore absence of Salmonella colorless: presence of propylene glycol— and β-galactosidase — bacteria, therefore absence of Salmonella.

In practice, bacteriological analyses carried out by the applicant using the Rambach medium gave the following results for 33 strains or species which can be divided into 12 Salmonella and 21 belonging to a genus other than Salmonella:

Salmonella (12):

+3 strains (1 *S. typhimurium*, 1 *S. paratyphi B*, and 1 *S. paratyphi C*) developed the expected red color, +1 strain (*S. arizonae*) developed an expected blue color, +8 strains (4 *S. typhi*, 1 *S. enterididis*, 1 *S. gallinarium*, 1 *S. pullorum* and 1 *S. paratyphi A*) remained colorless, other than Salmonella:

+1 strain (*Pseudomonas aeruginosa*) developed a red color.

While it is normal for the four *S. typhi* strains to remain colorless as already observed by Rambach, it is on the other hand abnormal to obtain negative tests for five other Salmonella species, two of which belonging to veterinary species (*S. gallinarum* and *S. pullorum*). Furthermore, one strain other than Salmonella leads to a positive result.

To summarize, the detection medium proposed by Rambach appears to be:

nonselective for the Salmonella genus since other bacteria, especially *Pseudomonas aegurinosa*, respond to the same test selective for some strains or species within the Salmonella genus since the *S. typhi* species in particular does not respond to the proposed test more appropriate for Salmonella of food or veterinary origin than that of clinical origin.

However, given the serious syndromes which Salmonella is capable of causing in man, including *S. typhi* which is responsible for typhoid fever, the development of a medium permitting differentiation of practically all Salmonella currently represents a real need.

SUMMARY OF THE INVENTION

The present invention aims to overcome the disadvantages described above.

More particularly, the subject of the present invention is a medium for the relatively reliable characterization of most of the Salmonella species encountered in practice during bacteriological examination, with a relatively low detection threshold.

The present invention arises from the discovery according to which:

species fermenting glucuronic acid and not producing β-galactosidase are very few in number; they are Salmonella (with the exception of *S. arizonae*), *Morganella morganii*, *Edwardsiella hoshinae*, *Edwardsiella tarda* and *Yersinia ruckeri* these latter three strains are very rarely isolated; consequently, the possibility of mistaking them for a Salmonella is very small in practice in practice *Morganella morganii* may be eliminated by the addition of inhibitors.

Consequently, according to the present invention, by combining glucuronic acid or a salt thereof and a pH indicator with the culture medium, in addition to the chromogenic or fluorigenic compound capable of being hydrolyzed by β-galactosidase, it is possible selectively to detect Salmonella, with the exception of *S. arizonae*, directly upon isolation.

Chromogenic or fluorigenic compound is understood to mean any marker whose molecule, in the presence of at least one specific enzyme, is capable of being hydrolyzed or cut into two parts, namely a nonchromogenic or nonfluorigenic inert part and a chromogenic or fluorigenic part that can develop a color which is visible with the naked eye or under UV light, directly or indirectly, that is to say by the action of an additional chemical compound called an indicator.

The efficacy of the chosen biochemical couple according to the present invention appears to be surprising in the sense that unlike most carbohydrates to which it belongs, glucuronic acid does not inhibit β-galactosidase with the exception of that produced by bacteria of the Serratia genus which is not expressed on the medium of the invention.

The medium according to the invention comprises a β-galactosidase-hydrolyzable chromogenic or fluorogenic compound which may be chosen from the following compounds: p-nitrophenyl β-D-galactopyranoside, 4-methylumbelliferyl β-D-galactopyranoside and 5-bromo-4-chloro-3indolyl β-D-galactopyranoside.

DESCRIPTION OF THE PREFERRED EMBODIMENTS

In a preferred embodiment of the medium according to the invention, the chromogenic compound is 5-bromo-4-chloro-3-indolyl β-D-galactopyranoside whose content by weight per liter of medium is preferably between 0.01 g and 1 g. This compound pigments the colonies of β-galactosidase-producing bacteria blue and has the advantage of limiting the color to the colonies without diffusion into the medium.

According to a specific composition of the medium of the invention, the medium contains a β-galactosidase inducer which may be chosen from lactose and isopropyl β-D-thiogalactopyranoside.

The preferred isoproypl β-D-thiogalactopyranoside content by weight is between 0 and 100 mg.

The medium according to the invention may contain at least one inhibitor of the growth of bacteria not belonging to the Salmonella species. This inhibitor may be at the same time an activator of the growth of Salmonella. It may be chosen from brilliant green, sodium deoxycholate and a mixture of bile salts. The preferred brilliant green and sodium deoxycholate contents per 1 l of medium are between 0 and 0.1 g and 0 to 10 g respectively.

The nutrient in the medium according to the invention consists of conventional ingredients which are essential for the development of bacteria. According to a specific mode of preparation of the medium of the invention, it consists of a peptone, a yeast extract and NaCl whose contents by weight per 1 l of medium are preferably between 1 and 20 g, 0 and 10 g and 0 and 10 g respectively.

According to a specific embodiment of the invention, the medium is provided in the form of solid agar, in which case the medium comprises agar whose content by weight per 1 l of medium is preferably between 5 and 25 g.

The medium according to the present invention contains glucuronic acid or a salt thereof. The medium preferably contains sodium glucuronate whose content by weight per 1 l of medium is preferably between 1 and 30 g.

The pH indicator present in the medium is chosen from phenol red, bromothymol blue, bromocresol purple and neutral red. In a preferred composition of the medium according to the invention, the pH indicator is neutral red whose content by weight per 1 l of medium is preferably between 5 and 100 mg.

Preferably, the pH of the identification medium is between 6 and 8.

In some cases, it was observed that after 24 hours of incubation of a Salmonella-containing sample on the medium of the invention, the specific color obtained for Salmonella may change due to realkalization of the medium. In particular, when the pH indicator is neutral red, the red color obtained, which is characteristic of the biochemical characteristics: absence of β-galactosidase and fermentation of glucuronic acid or its salt, may change to yellow.

To improve the culture medium according to the invention, the addition of at least one sugar which can be fermented by Salmonella was found to be necessary; this sugar is chosen from melibiose, sorbitol, dulcitol, mannitol, glucose and glucuronate and mixtures thereof, in an amount of between 1 and 10 g per liter of medium.

According to a preferred composition of the medium of the invention, the latter comprises sorbitol in an amount of between 5 and 10 g per liter, advantageously 8 g per liter.

In this latter composition, the sorbitol supplied to the medium may reveal bacteria of the Serratia genus as false positive.

In fact, these bacteria, which do not ferment glucuronic acid and which produce β-galactosidase which is not expressed on the medium of the invention in the absence of sorbitol, therefore remain colorless on the said medium but they can become colored red when the medium of the invention contains sorbitol. For a glucuronic acid composition less than or equal to 20 g/l of medium, 5-bromo-4-chloro-3-indolyl β-D-glucopyranoside (esculin) is added to the sorbitol-containing medium in an amount of between 0.01 and 0.05 g per liter of medium (and preferably 0.025 g); esculin gives a mauve or chestnut color to the Serratia colonies which may be present.

In the presence of sorbitol, the effect of inhibitors on the growth of bacteria of the Proteus and Morganella genera is reduced and the amount of bile salts should therefore be increased. Preferably, this amount is between 1 and 5 g of sodium deoxycholate, advantageously between 3 and 4 g per liter.

The preparation, implementation and advantages of a culture and detection medium according to the invention will now be illustrated by the following examples.

EXAMPLE 1

Preparation of a medium according to the invention

A composition of a medium of the invention is as follows:

| | | |
|---|---|---|
| bio-trypticase, bioMérieux | 5.00 g | |
| yeast extract, Difco | 3.00 g | |
| NaCl | 5.00 g | |
| neutral red | 0.03 g | |
| sodium deoxycholate | 3.00 g | |
| brilliant green | 0.01 g | |

-continued

| | | |
|---|---|---|
| sodium glucuronate | 12.00 g | |
| 5-bromo-4-chloro-3-indolyl β-D-galactopyranoside | 0.10 g | |
| isopropyl β-D-thiogalactopyranoside | 0.01 g | |
| agar | 15.00 g | |
| pH | 7.6 | |

The above ingredients, with the exception of sodium glucuronate, are dissolved in distilled water by maintaining the medium at boiling point for 1 minute, with stirring.

The solution thus obtained is autoclaved according to the usual sterilization methods (for example 120° C. for 15 min).

After autoclaving, the solution is cooled and maintained at 45° C. The sodium glucuronate is then added and dissolved. The complete medium is then distributed under sterile conditions into Petri dishes 90 mm in diameter in amounts of 20 ml per dish. Solidification is obtained after returning to room temperature. The dishes are stored at +4° C. until used.

EXAMPLE 2

Selective detection of Salmonella after culturing on a medium according to the invention The Petri dishes prepared above according to Example 1 are inoculated by the usual method.

The colonies formed on incubation for 24 hours at 37° C. are examined.

Depending on the color of the colonies, it is possible to determine the two biochemical characteristics of the bacteria, namely the production or nonproduction of β-galactosidase and the fermentation or nonfermentation of glucuronic acid or its salt:

brilliant red colonies: these are specific to bacteria which do not produce β-galactosidase and which ferment glucuronic acid or its salt blue colonies: these are specific to bacteria which produce β-galactosidase and which do not ferment glucuronic acid or its salt violet colonies: these are specific to bacteria which produce β-galactosidase and which ferment glucuronic acid or its salt.

colorless colonies: these are specific to bacteria which do not produce β-galactosidase and which do not ferment glucuronic acid or its salt, with the exception of bacteria of the Serratia genus which, although producing β-galactosidase, remain colorless because the enzyme is not expressed on the medium of the invention.

The brilliant red colonies are presumed to be Salmonella.

EXAMPLE 3

Preparation of a medium of the invention for the selective detection of Salmonella by observing the colonies after more than 24 hours of incubation.

Beyond 24 hours of incubation at 37° C., on the medium of Example 1, under the conditions of Example 2, the colonies with a brilliant red color tend to become yellow because of realkalization of the pH, thereby making the selective detection of Salmonella more difficult.

To prevent the change from red to yellow, a preferred composition of a medium of the invention is as follows:

| | |
|---|---|
| Pepticase | 2 to 8 g, preferably 3 g |
| Thione | 2 to 8 g, preferably 3 g |
| Meat extract | 0 to 3 g, preferably 3 g |
| Yeast extract | 0 to 3 g, preferably 2 g |
| Brilliant green | 0 to 0.01 g, preferably 0.003 g |
| Bile salts | 1 to 5 g, preferably 4 g |
| Neutral red | 0.025 g |
| Tris | 0.65 g |
| Sorbitol | 5 to 10 g, preferably 8 g |
| Sodium glucuronate | 6 to 15 g, preferably 12 g |
| 5-Bromo-4-chloro-3-indolyl β-D-galactopyranoside: | 0.17 g |
| Isopropyl p-D-thiogalactopyranoside: | 0.01 g |
| 5-Bromo-4-chloro-3-indolyl β-D-glucopyranoside: | 0.01 to 0.05 g, preferably 0.025 g |
| Agar | 14 g |
| pH | 7.6 |

EXAMPLE 4

Demonstration of the selectivity of a detection medium according to the invention The following 32 strains are examined:

3 *Escherichia coli* strains

2 *Serratia marcescens* strains

3 *Citrobacter freundii* strains

2 *Klebsiella pneumoniae* strains

2 *Klebsiella oxytoca* strains

4 *Salmonella enteritidis* strains

3 *Salmonella typhi* strains

3 *Proteus vulgaris* strains

3 *Proteus mirabilis* strains

3 *Staphylococcus aureus* strains

2 *Streptococcus pyogenes* strains

2 *Enterococcus faecalis* strains.

Each strain was cultured on a Petri dish, in the medium of the invention. The dishes were incubated at 36° C. for 20 hours. The colonies formed were visually examined.

Of the 32 isolates, all the Salmonella strains, and only these strains, gave red colonies, the characteristic appearance of Salmonella on the medium of the invention.

Blue colonies, indicating the presence of a β-galactosidase and the absence of glucuronic acid fermentation, were observed for one strain: that of *C. freundii.*

The 3 *E. coli* strains, the 4 Klebsiella strains and the 2 *C. freundii* strains gave violet colonies (combination of the 2 tests). The 6 Proteus were partially inhibited, with the presence of transparent colonies (absence of β-galactosidase and glucuronate fermentation).

None of the 7 staphylococcal, streptococcal and enterococcal strains developed on the medium.

This example clearly shows the specificity of this medium: only the Salmonella colonies exhibited a red pigmentation.

EXAMPLE 5

Comparison of the selectivity of the Salmonella-detection medium according to the invention with that of a medium commonly used.

The comparison is carried out between the medium described in Example 1 and the S.S. agar medium marketed by Diagnostics Pasteur. The latter, which is used for the selective isolation of Salmonella and Shigella, is based on the detection of the biochemical characteristics of bacteria linked to the fermentation of carbohydrates and to the production of H$_2$S.

Each of the 32 strains examined in Example 4 is cultured both on the medium according to the invention and on the S.S. medium.

On 24 hours of incubation at 37° C., the appearance of the colonies is examined. The colonies which are:

red on the medium according to the invention (strong presumption of Salmonella)

colorless (lactose negative) or with a black center (production of H$_2$S) on S.S. medium, are considered as suspect.

| No. of strains | SPECIES | MEDIUM ACCORDING TO THE INVENTION | S.S. AGAR |
|---|---|---|---|
| 3 | E. coli | 3 × violet | 3 × red |
| 2 | S. marcescens | 2 × colorless | 2 × colorless = SUSPICION |
| 3 | C. freundii | 2 × violet; 1 × blue | 3 × black center = SUSPICION |
| 2 | K. pneumoniae | 2 × violet | 2 × red |
| 2 | K. oxytoca | 2 × violet | 2 × red |
| 4 | S. enteritidis | 4 × red = SUSPICION | 4 × black center = SUSPICION |
| 3 | S. typhi | 3 × red = SUSPICION | 3 × colorless = SUSPICION |
| 3 | P. vulgaris | 3 × colorless | 3 × black center = SUSPICION |
| 3 | P. mirabilis | 3 × colorless | 3 × black center = SUSPICION |
| 3 | Staph. aureus | no growth | no growth |
| 2 | Strep. Pyogenes | no growth | no growth |
| 2 | Ent. faecalis | no growth | no growth |

Only 7 strains gave suspect red colonies on the medium according to the invention. They are all Salmonella.

On the other hand, on the S.S. medium, 18 strains were suspected as capable of being Salmonella, that is to say:

the 7 Salmonella (colorless colonies with a black center)

the 2 *S. marcescens* (colorless colonies)

the 3 *C. freundii* (colonies with a black center)

the 6 Proteus (colonies with a black center).

The selectivity of the detection medium according to the invention enables the number of verifications to be greatly reduced (7 against 18 with the S.S. medium) leading, for the use of this medium, to a saving of time and money compared with the use of a conventional medium.

EXAMPLE 6

Minimum threshold for the detection of Salmonella cultured on a medium according to the invention.

The test was carried out using the following 4 strains which were isolated on trypticase-soybean agar:

SE=*Salmonella enteritidis,*

ST=*Salmonella typhi*

EC=*Escherichia coli*

PA=*Escherichia coli*

PA=*Pseudomonas aeruginosa*

After culturing for 24 hours, at 37° C., on trypticase-soybean agar, a suspension in physiological saline is prepared for each strain and adjusted to point 1 of the Mac Farland scale, equivalent to about $2 \times 10^8$ bacteria per milliliter.

These suspensions are then diluted $10^4$-fold for EC and PA, and $10^4, 10^5, 10^6$-fold for SE and ST.

The various dilute suspensions of Salmonella are then mixed in equal volume with the dilute suspensions of EC or PA. Petri dishes containing the medium according to the invention are inoculated with each of the mixtures obtained, by means of a calibrated dose of 10 microliters.

On 24 hours of incubation at 37° C., the number of Salmonella colonies and that of non-Salmonella colonies are counted on each dish.

The results are presented in the table below.

| Dilutions of the Salmonella/ non-Salmonella mixture | Number of Salmonella/non-Salmonella colonies | | | |
|---|---|---|---|---|
| | SE/EC | SE/PA | ST/EC | ST/PA |
| $10^4/10^4$ | 125/97 | 91/118 | 142/160 | 83/136 |
| $10^5/10^4$ | 15/117 | 11/85 | 10/121 | 7/99 |
| $10^6/10^4$ | 1/110 | 2/94 | 1/133 | 0/105 |

These results demonstrate the very low detection threshold for Salmonella in the medium according to the invention: it is indeed possible easily to identify down to one colony of Salmonella (red) among a hundred or so colonies of bacteria not belonging to this genus: EC colonies are detected by a violet color and PA colonies are colorless. Furthermore, the red pigmentation of the Salmonella colonies is constant irrespective of their number on the isolation medium.

We claim:

1. A method of bacteriological analysis for the selective detection of Salmonella in an analytical sample, comprising:
   growing the analytical sample on an identification medium comprising a nutrient that is metabolized by said Salmonella, a chromogenic or fluorigenic compound capable of being hydrolyzed by the enzyme β-galactosidase, glucuronic acid or a salt thereof and a pH indicator; and
   both a) detecting the absence of production of a chromogenic or fluorigenic part and b) detecting with said pH indicator the fermentation of glucuronic acid or a salt thereof.

2. The method of claim 1, wherein the identification medium comprises sodium glucuronate in an amount of between 1 and 30 g per one liter of identification medium.

3. The method as claimed in claim 1, wherein the identification medium comprises, in addition, at least one sugar which can be fermented by Salmonella, selected from the group consisting of melibiose, sorbitol, dulcitol, mannitol, glucose and glucuronate in an amount of between 1 and 10 g per liter.

4. The method of claim 1, wherein the pH is adjusted to a value of between 6 and 8.

5. A medium for the culture and selective detection of bacteria of the Salmonella genus, except for the species S. ariconae comprising a nutrient which is metabolized by said bacteria and a chromogenic or fluorigenic compound capable of being hydrolyzed by the enzyme β-galactosidase, wherein the medium comprises, in addition, glucuronic acid or a salt thereof and a pH indicator.

6. The medium of claim 5, wherein the amount of glucuronic acid or its salt is between 1 and 30 g per liter of medium.

7. The medium of claim 5, which comprises, in addition, at least one sugar which can be fermented by Salmonella, chosen from melibiose, sorbitol, dulcitol, mannitol, glucose and glucuronate, in an amount of between 1 and 10 g per liter.

8. The medium of claim 7, which comprises sorbitol in an amount of between 5 and 10 g per liter, and preferably 8 g per liter.

9. The medium of claim 7, which comprises, in addition, 5-bromo-4-chloro-3-indolyl glucopyranoside in an amount of between 0.01 and 0.05 g per liter of medium, preferably 0.025 g.

10. The medium of claim 5, wherein the chromogenic or fluorigenic compound is chosen from the following compounds, namely p-nitrophenyl β-D-galactopyranoside, 4-methylumbelliferyl β-D-galactopyranoside and 5-bromo-4-chloro-3-indolyl β-D-galactopyranoside.

11. The medium of claim 10, wherein the chromogenic compound is 5-bromo-4-chloro-3-indolyl β-D-galactopyranoside.

12. The medium of claim 11, wherein the amount of 5-bromo-4-chloro-3-indolyl β-D-galactopyranoside is between 0.01 and 1 g per liter.

13. The medium of claim 5, which comprises an inhibitor of the growth of genera or species other than Salmonella, chosen from the group comprising brilliant green, sodium deoxycholate and a mixture of bile salts.

14. The medium of claim 13, which comprises brilliant green in an amount of between 0 and 100 mg, and sodium deoxycholate in an amount of between 0 and 10 g.

15. The medium as claimed in claim 14, wherein the amount of sodium deoxycholate is between 1 g and 5 g, preferably between 3 and 4 g per liter of medium and the medium comprises sorbitol in an amount of between 5 and 10 g per liter.

16. The medium of claim 5, wherein the nutrient comprises a peptone, a yeast extract and sodium chloride, the amounts of which are between 1 and 20 g, 0 and 10 g and 0 and 10 g, respectively.

17. The medium of claim 5, wherein the pH indicator is chosen from the following compounds, namely phenol red, bromothymol blue, bromocresol purple and neutral red.

18. The medium of claim 17, wherein the pH indicator is neutral red, in an amount of between 5 and 100 mg.

19. The medium of claim 5, which comprises a β-galactosidase inducer, namely lactose or isopropyl β-D-thiogalactopyranoside.

20. The medium of claim 19, wherein the β-galactosidase inducer is isopropyl β-D-thiogalactopyranoside, in an amount of between 0 and 100 mg per liter of medium.

21. The medium of claims 5 to 20, wherein its pH is adjusted to a value of between 6 and 8.

22. The medium of claim 5, wherein said medium is provided in the form of solid agar.

23. A kit for bacteriological characterization, comprising a package of a medium as of claim 5.

* * * * *